Figure 1:
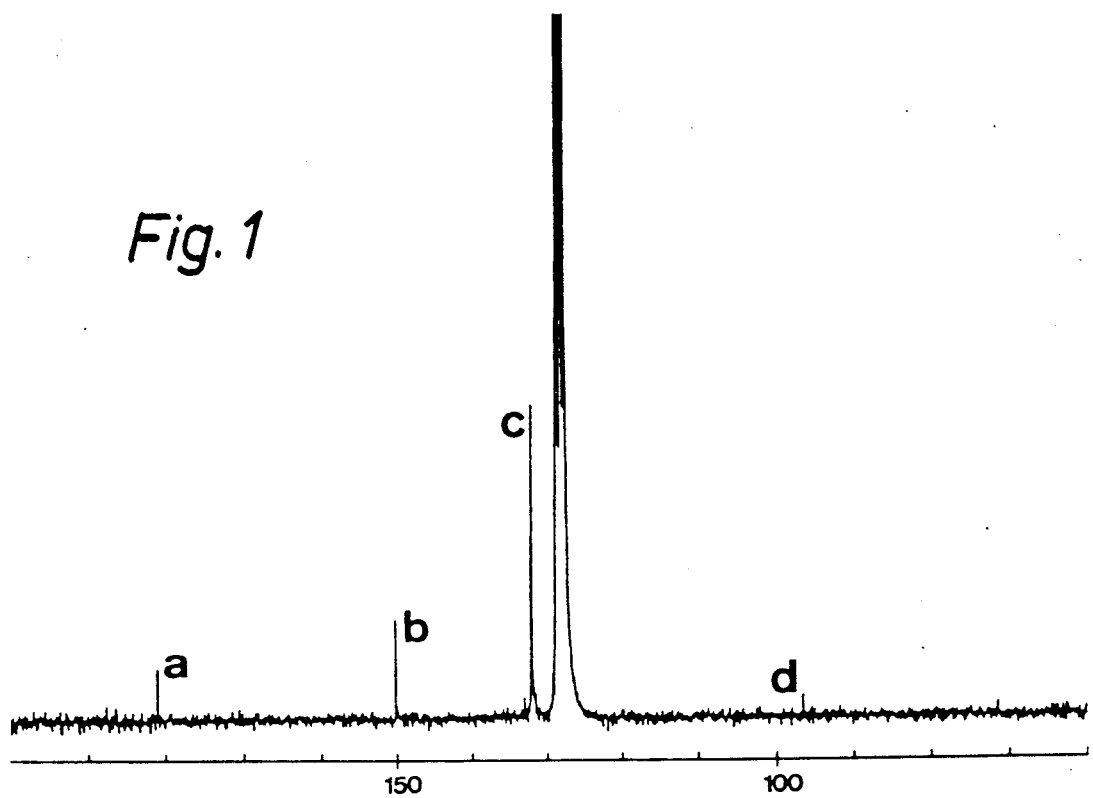

United States Patent [19]

Simon et al.

[11] Patent Number: 5,037,968

[45] Date of Patent: Aug. 6, 1991

[54] ADDUCTS OF AN ANION OF AN OXA ACID AND A KETO COMPOUND, PROCESS FOR THE PREPARATION OF SAID ADDUCTS, AND PROCESS FOR THE DETERMINATION OF THE CONCENTRATION OF THE ANIONS OF OXA ACIDS USING SAID KETO COMPOUNDS

[75] Inventors: Wilhelm Simon, Zurich; Erno Pretsch, Meilen, both of Switzerland

[73] Assignee: Willi Moller, Zurich, Switzerland

[21] Appl. No.: 166,868

[22] Filed: Mar. 11, 1988

[30] Foreign Application Priority Data

Mar. 13, 1987 [CH] Switzerland ............................ 939/87
Sep. 30, 1987 [CH] Switzerland ........................ 3801/87

[51] Int. Cl.$^5$ ...................... C09B 29/01; C09B 29/34; G01N 21/25; C09K 19/24
[52] U.S. Cl. .................................. 534/851; 534/577; 534/588; 534/595; 534/596; 534/650; 534/653; 534/751; 534/770; 534/789; 534/790; 436/164; 436/172
[58] Field of Search ................... 534/851, 588, 573 R, 534/650, 653, 751, 770, 789, 790

[56] References Cited

U.S. PATENT DOCUMENTS

| | | | |
|---|---|---|---|
| 2,108,824 | 10/1938 | McNally et al. | 534/851 X |
| 2,206,099 | 7/1940 | McNally et al. | 534/851 |
| 2,206,911 | 7/1940 | McNally et al. | 534/851 |
| 2,217,693 | 10/1940 | McNally et al. | 534/851 X |
| 2,516,302 | 7/1950 | Dickey | 534/851 X |
| 3,429,785 | 2/1969 | Ross | 204/1 |
| 3,723,281 | 3/1975 | Wise | 204/195 L |
| 3,968,168 | 7/1976 | Strong | 260/612 R |

FOREIGN PATENT DOCUMENTS

| | | | |
|---|---|---|---|
| 0729595 | 12/1942 | Fed. Rep. of Germany | 534/851 |
| 1920176 | 10/1970 | Fed. Rep. of Germany | 260/612 R |
| 0197283 | 7/1938 | Switzerland | 534/851 |
| 0200251 | 12/1938 | Switzerland | 534/851 |
| 0200252 | 12/1938 | Switzerland | 534/851 |
| 0200254 | 12/1938 | Switzerland | 534/851 |

OTHER PUBLICATIONS

Fialkov et al. I, Chemical Abstracts, vol. 65, 8796 to 8797 (1966).
Fialkov et al. II, Index Chemicus, vol. 22, #67413 (1966).
Behringer et al., Chemical Abstracts, vol. 109, No. 22591q (1988).
Greenberg, J. A., Meyerhoff, M. E., Anal. Chim. Acta. 1982, 141, 57–64.
Scott et al., Clin. Chem. (Winston-Salem, N.C.) 1986, 32, 137–141.
Smirnova, A. L. et al., Electrokimiya, 1985, 21, 1221–1224.
Meyerhoff, M. E. et al., Analytical Chemistry, 1987, 59, 144.
Kraft, H. G. et al., Inorganica Chimica Acta., 1980, 47, 41–45.
Journal of Organic Chemistry, vol. 44, No. 9, 1979, 1577–1578, Finiels et al.
Bull. Chem. Soc. Japan, vol. 55, 1982, 641, Ogura et al.

*Primary Examiner*—Mary C. Lee
*Assistant Examiner*—Fiona T. Powers
*Attorney, Agent, or Firm*—Seidel, Gonda, Lavorgna & Monaco

[57] ABSTRACT

Keto compounds in which to the carbon atom in the neighboring position to the keto compounds there is bonded at least one strongly electron attracting substituent and/or in which there is conjugating with the carbon-oxygen-double bond of the keto group a π-electron system have the ability of interacting selectively with the anions of oxa acids yielding adducts, chelates or complexes.

Provided that in the corresponding keto compounds the keto group is a part of a chromophore, then the shifting of the absorption in the visible range or the ultraviolet range of the wave lengths is observed, compared with the corresponding absorption of the free keto compound.

The corresponding keto compounds are used for the determination of the anions of the oxa acids and they e.g. can be the ion sensitive component of a corresponding ions sensitive part for the determination of said anions. Several of said keto compounds can be also used as color indicator for the anions of the oxa acids.

7 Claims, 3 Drawing Sheets

ADDUCTS OF AN ANION OF AN OXA ACID AND A KETO COMPOUND, PROCESS FOR THE PREPARATION OF SAID ADDUCTS, AND PROCESS FOR THE DETERMINATION OF THE CONCENTRATION OF THE ANIONS OF OXA ACIDS USING SAID KETO COMPOUNDS

BACKGROUND OF THE INVENTION

Organic compounds which are able to form lipophilic complexes with cations, like certain dicarboxylic acid diamides, are frequently used for the determination of cations in sample solutions. For example, corresponding ion selective parts like ion selective membranes of ion selective electrodes which contain as a component the organic compound which is able to form the complex with the cations are frequently used for the determination of the concentration of said cations in sample solutions. Corresponding equipment for the determination of the concentration of sodium ions, potassium ions and calcium ions in body fluids, like whole blood or blood serum, have been used for several years in the clinical field for the determination of said cations.

Furthermore, test devices are known in the art which contain said cation selective complex forming organic components are well as an indicator; for instance a pH indicator, in a carrier material or on a carrier material.

In said test devices an alternation of a property of the indicator is determinable, for instance a colour change of the indicator, if the test devices are contacted with a sample solution which contains the cation to be determined.

Contrary to this, in the prior art only a few organic compounds are described which have the ability of selectively interacting with anions and are useful as ion selective components for the determination of the stated anions in sample solutions, e.g. a quantitative or semi-quantitative determination of the concentration of the anions in said sample solutions.

It was the aim of the present invention to select from compounds which are already described in the prior art, such compounds which are able to interact selectively with anions of oxa acids, respectively to provide new compounds which have the ability of interacting with anions of oxa acids.

DESCRIPTION OF THE PRIOR ART

For the determination of the concentration of anions, mainly lipophilic ammonium compounds have been used as ion selective components.

In the U.S. Pat. No. 3,429,785 there are described anion selective electrodes which contain in a liquid phase which is essentially water immiscible a quaternary salt of an aliphatic amine.

In the U.S. Pat. No. 3,723,281 there are described electrodes which have a sensitivity for bicarbonate anions, in which the ion sensitive membrane contains as an ion selective component a quaternary ammonium salt having a high molecular weight, dissolved in a solvent system, which contains an organic compound and an aliphatic alcohol having 6–12 carbon atoms. Said aliphatic compound is usually a fluorinated alcohol or an ester of said fluorinated alcohol. However trifluoroacetylbenzenes in which the benzene nucleus is substituted with one or two alkyl groups are also mentioned. There is stated in said U.S. patent that it is believed that the ion sensitive component of the membrane is the quaternary amine, while the stated organic compounds merely act as modifying components.

Further developments of said electrodes of the above stated U.S. patent are described in the publication of Greenberg, J. A. Meyerhoff, M. E. in Anal. Chim. Acta 1982, 141, 57–64, as well as in the publication of Scott et al. in Clin. Chem. (Winston-Salem, N.C.) 1986, 32, 137–41 and furthermore in the publication of Smirnova, A. L. et al. in Electrokimiya 1985, 21, 1221–1224. Said electrodes can be used for the determination of carbon dioxide in blood serum and blood plasma.

In most recent times it was found out that the trifluoroacetyl-p-butylbenzene, which had already been mentioned as a solvent component of the carbonate selective electrodes in U.S. Pat. No. 3,723,281, has itself the ability of forming adducts with carbonate anions. Said trifluoro keto compound is able to form adducts of one mole carbonate anion with one mole of said fluorinated keto compound, and is also able to form adducts of one mole of carbonate anion and two moles of said fluorinated keto compound. With regard to this we refer to the publication of Meyerhoff M. E., Pretsch E., Welti D. H. and Simon W. in Analytical Chemistry, 1987, 59, 144.

In the publication of H. G. Kraft and B. M. Rode in Inorganica Chimica Acta, 47 (1980), pages 41–45, chelate complexes of the cations lithium, sodium, magnesium and calcium with the lower aliphatic diketones, diacetyl, acetyl acetone and acetonyl-acetone, were investigated. The salts of the cations which were tested were the corresponding perchlorates and it was found out that from the tested diketones that only the acetyl-acetone was able to form complexes with said cations. In said publication no interaction is mentioned, like complex formation, between the anions of the corresponding salts, i.e. the perchlorate anions, and the diketones.

In a publication in the J. Org. Chem. vol. 44 no. 9, 1979, pages 1577–1578, the reactivity of certain monoketones with regard to nucleophilic reagents, was investigated and among said nucleophilic reagents also the reactivity with regard to the anions of two oxa acids, i.e. the sulfite anions and the chromate anions. Totally 26 ketones were tested and in the tested monoketones the keto group was a member of a cycloaliphatic ring structure. In none of the tested ketones was there in the neighbour position to the keto group a carbon atom to which at least one strongly electron attracting substituent was bonded. Also in none of the tested keto compounds was a $\pi$-electron system conjugating with the carbon-oxygen-double bond of the keto group.

Several keto compounds are described in the prior art in which to the carbon atom in the neighbouring position of the keto group there is bonded at least one strongly electron attracting substituent. For instance there are described in the U.S. Pat. No. 3,968,168 such 1,1-diphenyl alkanes which have an insecticidal activity. For the preparation of said compounds there can be used monophenyl substituted ketones, for example also corresponding ketones in which to the carbon atom in the neighbouring position to the carbonyl group there are bonded one to three chlorine atoms.

In the German Offenlegungsschrift No. 1 920 176 there is described a process for the preparation of hydroxy crotonic acid lactones and as starting material there can be used according to said process also bromo substituted phenones.

In a publication in the Bull. Chem. Soc. JPN, vol. 55, 1982, page 641, the use of selenium oxide as a mild oxydating agent was tested and in said publication also a diketo compound in which the keto groups are in neighbouring position to each other is described.

DESCRIPTION OF THE INVENTION

The present invention concerns such keto compounds which have the ability of selectively interacting with the anions of oxa acids and the invention, furthermore, concerns the adducts of said keto compounds with the anions of the oxa acids.

The keto compounds which according to the present invention have the ability of selectively interacting with the anions of oxa acids comprise at least one keto group in which
either to the carbon atom in the neighbour position to said keto group there is bonded at least one strongly electron attracting substituent and/or
which keto compound comprises a $\pi$-electron system which is conjugating with the carbon-oxygen-double bond of the keto group or one of the keto groups or
which keto compound comprises at least two keto groups which are in neighbouring position to each other or in such a position to each other that the two keto groups are able to form with the anion of the oxa acid a cyclic chelate,
with the provision that, however, in those monoketo compounds in which the keto group is bonded to an alkyl substituted benzene nucleus the group in neighbouring position to said keto group must not be a trifluoro methyl group.

Through the disclaimer stated above such monoketo compounds will be excluded from the scope of protection, in which the keto group is bonded to an alkyl substituted phenyl nucleus and in which to the keto compound there is furthermore bonded a trifluoro methyl group. Said compounds were disclaimed from the scope of protection, because in the publication in Analytical Chemistry, 1987, 59, 144, which was mentioned before, there is already disclosed that the trifluoro acetyl-p-butylbenzene is able to form adducts with a certain anion of an oxa acid, i.e. with the carbonate anion.

The monoketo compounds which according to the present invention have the ability to interact with the anions of oxa acids and which for example form adducts or complexes with said anions of oxa acids, have to have either in the neighbouring position to the keto group a carbon atom to which at least one strongly electron attracting substituent is bonded or said keto compounds have to comprise a $\pi$-electron system which is conjugating with the carbons-oxygen-double bond of the keto group or said keto compounds have to be corresponding keto compounds which comprise at least two keto groups which are in the above mentioned positions with regard to each other.

Preferred strongly electron attracting substituents, which are bonded to the carbon atom in the neighbouring position of the keto group are halide atoms and nitro groups, preferably bromine atoms, chlorine atoms and fluorine atoms.

Examples of $\pi$-electron systems which conjugate with the carbon-oxygen-double bond of the keto group or at least one of the keto groups of the keto compounds forming the inventive adducts with the anions of oxa acids, are preferably $\pi$-electron systems of an aromatic carbocyclic compound or a heterocyclic compound of aromatic character or the $\pi$-electron system of the carbon-carbon-double bond of a conjugated polyene or the $\pi$-electron system of the carbon-carbon-triple bond of a conjugated polyine or the $\pi$-electron system of an azo group.

Preferred anions which are able to interact selectively with the keto compounds in question, respectively the preferred anion component of inventive adducts of anions and keto compounds are the anions of the following oxa acids:

$CO_3^{--}$, $HCO_3^-$, $SO_4^{--}$, $HSO_4^-$, $SO_3^{--}$, $HSO_3^-$, $PO_4^{---}$, $HPO_4^{--}$, $H_2PO_4^-$, $ClO_3^-$, $ClO_4^-$, $BrO_3^-$, $IO_3^-$, $NO_3^-$, $NO_2^-$, $CrO_4^{--}$, $HCrO_4^-$, $Cr_2O_7^{--}$ or $HCr_2O_7^-$ or the anions of carboxylic acids, hydroxycarboxylic acids, keto-carboxylic acids, aminocarboxylic acids or the anions of peptides or the anions of organic derivatives of a phosphoric, diphosphoric or triphosphoric acid, preferably the esters of the phosphoric, the diphosphoric or triphosphoric acids, preferably an adenylic acid, the adenosine diphosphate or adenosine triphosphate.

A further class of keto compounds, which according to the present invention is able to interact selectively with the anions of oxa compounds are those keto compounds which comprise at least two keto groups, which keto groups are either in neighbouring position to each other or are in such a position to each other that they are able to form a cyclic chelate between both keto groups and the anion of the oxa acid.

Preferred such diketo compounds which according to the present invention interact with the anions of oxa acids respectively preferred keto components of the adducts between the keto compound and the anion of the oxa acid, are 1,2-diketo compounds which correspond to the following formula IV:

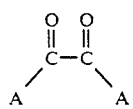

IV in which diketo compounds the groups ·

A are selected independently from each other from the group comprising saturated or unsaturated aliphatic or alicyclic, aromatic or heterocyclic radicals, which are substituted or unsubstituted or both groups A together close the compounds of formula IV to a carbocyclic or heterocyclic ring structure comprising 5-7 members of the ring, which ring structure comprises at least one double bond which is conjugating with the carbon-oxygen-double bond of at least one of the two carbonyl groups and wherein the ring system optionally furthermore comprises condensed aromatic or heteroaromatic rings, and which aliphatic, alicyclic, aromatic or heterocyclic radicals or carbocyclic or heterocyclic ring structures are unsubstituted or substituted with one or more substituents selected from the group comprising alkyl groups, substituted alkyl groups, alkenyl groups, substituted alkenyl groups, nitro groups, ether groups, ester groups, amino groups, monoalkyl amino groups, dialkylamino groups, monoaryl amino groups, diarylamino groups, azo groups or halide atoms.

It is, furthermore, possible that in said 1,2-diketo compounds of the formula IV one of the two keto groups or both keto groups of said diketo compounds of formula IV are a part of a chromophore and in this case the light absorption of the adduct of the keto compound of formula IV with the light absorption of the corresponding free keto compound.

Said shifting of the light absorption can be either in the visible range or in the ultraviolet range. Usually the adduct of the diketo compound with an anion of the oxa acids has a light absorption which is shifted into the direction of shorter wave lengths, compared with the light absorption of the free 1,2-diketo compound of formula IV, i.e. the shifting of the light absorption is a hypsochromic shifting. Accordingly, a free keto compound of formula IV which is coloured orange or red, usually will yield an adduct with an anion of a keto acid which is coloured yellow or whitish.

It, however, is also possible that the light absorption of the adduct of the keto compound of formula IV with the anion of the oxa acid is shifted in the visible range or in the ultra violet range in direction to an absorption in the range of longer wave length, compared with the light absorption of the corresponding free keto compounds of formula IV, i.e. it is also possible that an bathochromic shifting of the light absorption occurs.

The 1,2-diketo compounds of formula IV can also comprise in their structure a fluorescent group. In this case a difference in the fluorescence between the free keto compounds of formula IV and the adduct of the keto compound of formula IV with an anion of an oxa acid can be detected. Through the formation of the adduct between the corresponding keto compound of formula IV and the anion of the oxa acids either a fluorescence of the free keto compounds of formula IV is quenched or in a corresponding not fluorescent free keto compound of formula IV through the formation of the adduct between said keto compound and the anion of the oxa acid a fluorescence is induced.

Preferred examples for cyclic 1,2-diketo compounds of formula IV are the corresponding 1,2-benzoquinone compounds of formula IX

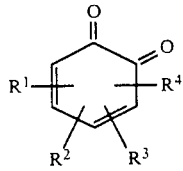

IX in which the radicals $R^1$, $R^2$, $R^3$ and $R^4$ are independently from each other selected from the group comprising hydrogen atoms, alkyl groups, cycloalkyl groups, alkenyl groups, alkinyl groups, azo-groups, nitro groups, halogen atoms, aromatic or heteroaromatic ring systems, which are either directly bonded to the benzoquinone structure or which are bonded to the benzoquinone structure through an azo-group or an alkylen group and wherein the said saturated or unsaturated aliphatic, alicyclic, aromatic or heteroaromatic radicals are either unsubstituted or substituted, for instance substituted with halide atoms, optionally substituted alkyl groups, nitro groups or azo-groups or in which compounds of formula IX the radicals $R^1$, $R^2$, $R^3$ and $R^4$ form together with the carbon atoms to which they are bonded one or more condensed aromatic or heteroaromatic rings or ring systems and said rings or ring systems can be unsubstituted or substituted, e.g. with substituents selected from the group comprising halide atoms, alkyl groups, halosubstituted alkyl groups, nitro groups or azo-groups.

Preferred examples for 1,2-benzoquinones of formula IX are such compounds, in which 1, 2 or 3 of the radicals $R^1$, $R^2$, $R^3$ and $R^4$ are hydrogen atoms while 1, 2 or 3 of the radicals $R^1$, $R^2$, $R^3$ and $R^4$ are alkyl groups having 1–8 carbon atoms or halosubstituted alkyl groups having 1–8 carbon atoms. An examples for an 1,2-benzoquinone of said group is the 3,5-di-tert.butyl-1,2-benzoquinone.

Examples for 1,2-benzoquinones of formula IX, in which two of the radicals $R^1$, $R^2$, $R^3$ and $R^4$ are in neighbouring position to each other and form together with the carbon atoms to which they are bonded, condensed rings or ring systems, are 1,2-naphthoquinones and 9,10-phenanthra quinones. To the aromatic rings of said compounds optionally further substituents can be bonded.

A further example for a cyclic 1,2-diketo compound of formula IX are the azenaphthen quinones having the following formula X

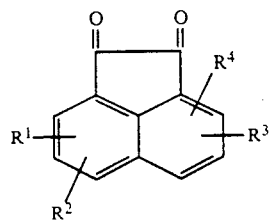

X and in said compounds of formula X the radicals $R^1$, $R^2$, $R^3$ and $R^4$ have the same meaning as already outlined before for the 1,2-benzoquinone compounds of formula IX.

Examples for 1,3-diketo compounds, in which the anions of the oxa acid is able to form a cyclic chelate with the two keto compounds, are the compounds having the following formula XI

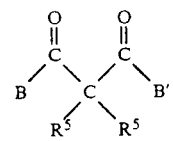

XI in which the radicals $R^5$ are independently from each other selected from the group which comprises hydrogen atoms, haline atoms, alkyl groups, alkenyl groups, cycloalkyl groups, aromatic radicals, heteroaromatic radicals, nitro groups and azo-groups and in which at least one of the radicals B or B' comprises a π-electron system which is conjugating with the carbon-oxygen-double bond of the keto group to which said group B or B' is bonded, and/or that in at least one of the radicals B or B' there is bonded to a carbon atom, which is connected with the carbonyl group, at least one strongly electron attracting substituent. Typical examples for such 1,3-diketo compounds of formula XI are those, in which at least one of the radicals B or B' is a group having the structure Ar—, Ar—O—, Ar—N=N— or Ar—CH=CH wherein Ar is a substituted or unsubstituted aromatic residue comprising one or more nuclei of a substituted or unsubstituted heterocyclic radical of aromatic character comprising one or more nuclei.

In the same way as it was already outlined before with regard to the 1,2-diketo compounds of formula IV also in the case of the 1,3-diketo compounds of formula XI at least one of the two keto groups can be a part of a chromophore or the compounds of formula XI can comprise a group which is fluorescent or in which fluorescence can be induced. In said compounds of formula XI the light absorption of the free 1,3-diketo compounds of formula XI differs in the visible range of the wave length or in the ultraviolet range of the wave length from the light absorption of the adduct of said 1,3-diketo compounds of formula XI with the anions of the oxa acids or through the formation of the adduct of the 1,3-diketo compounds of formula XI with the anion of an oxa acid a fluorescence is provoked or a fluorescence is quenched.

As already outlined before in diketo compounds the two keto groups can be in a more distant position to each other than the position 1,3, provided that the anion of the oxa acid is able to form a cyclic chelate with the two carbonyl groups. As examples for diketo compounds of said class there are mentioned anthracene-derivatives, in which the two keto groups are bonded to the position 1 and 8 of the anthracene structure. Said compounds, accordingly, have a basic structure which is outlined by the following formula XII

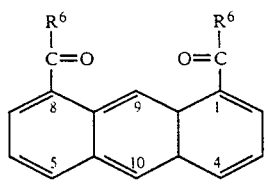

XII and also here to the aromatic nuclei of the anthracene derivative one or more substituents can be bonded, like e.g. the radicals $R^1$, $R^2$, $R^3$ and $R^4$, which have the meaning which already had been outlined before with regard to the 1,2-diketo compounds having the formulae IV, IX and X.

The radicals $R^6$ of said diketo compounds are organic radicals and preferably to the carbon atom which is attached to the carbonyl group there is bonded at least one strongly electron attracting substituent.

Also in the diketo compounds of formula XII at least one of the two keto groups can be a part of a chromophore or the diketo compounds of formula XII can comprise a group which has the ability of fluorescence. In the same way as it had already been explained before also in the compounds of formula XII the light absorption of the adduct of the diketo compound of formula XII with the anions of the oxa acids in the visible range or in the ultraviolet range is shifted, compared with the light absorption of the free keto compound of formula XII. If the compounds of formula XII comprise a group which has the ability of fluorescing, then the fluorescence can be produced or quenched, when the free diketo compound of formula XII forms the adduct with the anion of an oxa acid.

It was already explained before that the keto compounds which according to the present invention interact with the anions of oxa acids respectively in the inventive adducts of keto compounds with the anions of oxa acids, the corresponding keto compound has to comprise at least one keto group in which to the carbon atom in the neighbouring position to said keto group there is bonded at least one substituent which is strongly electron attracting and/or that said keto compound comprises a π-electron system which is conjugating with the carbon-oxygen-double bond of the keto group. Keto compounds which are able to form the inventive adducts with the anions of the oxa acids, however, also can comprise two or more such isolated keto groups, which are bonded to the molecular structure so that said two keto groups are not able to form a cyclic chelate with the anions of the oxa acids. An example for such a diketo group having said isolated keto groups is an azo compound having the following formula XIII

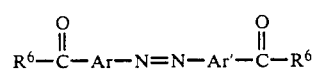

XIII in which the radicals

Ar and Ar' are independently from each other selected from a group comprising substituted or unsubstituted aromatic radicals which comprise one or several nuclei and substituted or unsubstituted heterocyclic radicals of aromatic character, which comprise one or more nuclei and in which compounds of formula XIII the radicals $R^6$ are organic radicals, preferably radicals in which to the carbon atoms of said radical which is bonded to the keto group there is bonded at least one substituent which is strongly electron attracting. If in said keto compounds of formula XII the radical Ar and also the radical Ar' is a phenyl radical, then said compounds for instance can have the following structure:

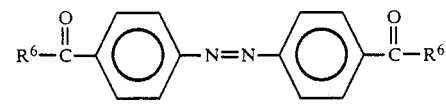

and in said keto compounds optionally to the benzene nuclei there can be bonded further substituents like for instance radicals having the same meaning as the radicals $R^1$, $R^2$, $R^3$ and $R^4$ which had been already defined with regard to the diketo compounds having the formulae IX and X.

A specially preferred class of keto compounds which according to the present invention interact with the anions of oxa acids, respectively a specially preferred keto component of the inventive adducts of anions of oxa acids and keto compounds are those keto compounds which comprise at least one keto group in which to the carbon atom in the neighbouring position to said keto group there is bonded at least one strongly electron attracting substituent and which keto compounds furthermore comprise a π-electron system which is conjugating with the carbon-oxygen-double bond of said keto group.

In said specially preferred above mentioned keto compounds and also in the diketo compounds of formulae XI and XII the carbon atom, to which at least one strongly electron attracting substituent is bonded, is preferably a group having the following formula

in which the radicals $X^1$, $X^2$ and $X^3$ are independently from each other selected from the group comprising hydrogen atoms, alkyl groups, alkenyl groups, alkinyl groups, fluorine atoms, chlorine atoms, bromine atoms, iodine atoms or nitro groups, however, with the provision that at least one of the substituents $X^1$, $X^2$ and $X^3$ is a strongly electron attracting substituent selected from the group which comprises fluorine atoms, chlorine atoms, bromine atoms or nitro groups.

In the above stated specially preferred monoketones, in which a $\pi$-electron system is conjugating with the carbonyl group and in which furthermore to the carbon atom in the neighbouring position to the carbonyl group there is bonded at least one strongly electron attracting substituent, said carbon atom is preferably a group of the above stated formula. The same is also true for the diketo compounds mentioned before and, accordingly, also in the diketo compounds of formulae XI, XII and XIII the residues B, B' and $R^6$ respectively are preferably groups which correspond to the above stated formula.

Specially preferred keto compounds which according to the present invention have the ability of selectively interacting with the anions of oxa acids, respectively specially preferred keto components of the inventive adducts of the keto compounds with anions of oxa acids are accordingly the compounds of formula I

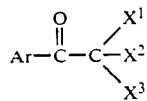
                                 I in which Ar is a substituted or unsubstituted aromatic system comprising one or more nuclei or a substituted or unsubstituted heterocyclic system of aromatic character which comprises one or more nuclei and $X^1$, $X^2$ and $X^3$ are independently from each other selected from the group comprising hydrogen atoms, alkyl groups, alkenyl groups, alkinyl groups, aryl groups, fluorine atoms, chlorine atoms, bromine atoms, iodine atoms or nitro groups, wherein however at least one of the substituents $X^1$, $X^2$ and $X^3$ is a strongly electron attracting substituent selected from the group comprising fluorine atoms, chlorine atoms, bromine atoms or nitro groups and with the further provision that in those compounds of formula I wherein Ar is an alkyl substituted phenyl nucleus, one of the radicals $X^1$, $X^2$ and $X^3$ has to have an other meaning than that of a fluorine atom.

In said compounds of formula I the aromatic or heteroaromatic ring systems are preferably selected from the group which comprises phenyl, naphthalene, anthracene, thiophene, furane, pyrrole, indole, benzofurane, benzothiophene, pyridine, chinoline, pyrazine or triazine. Furthermore the aromatic or heteroaromatic ring systems are substituted or unsubstituted and in the corresponding substituted aromatic or heteroaromatic ring systems, like the above stated preferred ring systems, the substituents are preferably selected from the group which comprises:

halide atoms, nitro groups, thiol groups, azo groups, ether groups, carboxylic acid ester groups, hydroxy groups, esterified hydroxy groups, amino groups, alkylamino groups, in which the alkyl radicals are optionally substituted alkyl groups, dialkylamino groups in which the alkyl radicals are optionally substituted alkyl radicals, arylamino groups, respectively diarylamino groups in which the aryl radicals are optionally substituted aryl radicals, cycloalkylamino groups, respectively dicycloalkylamino groups in which the cycloalkyl groups are optionally substituted cycloalkyl groups, alkyl groups, substituted alkyl groups, alkenyl groups, substituted alkenyl groups, alkinyl groups, substituted alkinyl groups, cycloalkyl groups, substituted cycloalkyl groups, aryl groups and substituted aryl groups.

Preferred examples for the group having the formula

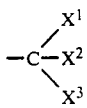

are the following:
the monochloromethyl group, dichloromethyl group, trichloro methyl group, monofluoromethyl group, difluoromethyl group, monochloromonofluoro methyl group, monochlorodifluoro methyl group, dichloromonofluoro methyl group as well as also those of the above stated chloro containing, respectively chloro and fluoro containing groups in which one or more of the chloro atoms are substituted by bromo atoms. Said specially preferred groups for instance can occur in the compounds having the formulae XI, XII, XIII and also in the compounds of formula I. A further preferred meaning of the groups of the above stated formulae is the trifluoro methyl group, however in those compounds of formula I, wherein Ar is an alkyl substituted benzene nucleus, the above stated groups must not be a trifluoro methyl group.

Preferred examples for keto compounds having the above stated formula I, in which the radical Ar is a benzene nucleus which is unsubstituted or substituted, are the following compounds:

trifluoroacetophenones, in which the benzene nucleus is unsubstituted or substituted with one or more halide atoms, nitro groups, azo groups or halo substituted alkyl groups like e.g. trifluoromethyl groups; monochloroacetyl benzene, dichloroacetyl benzene and trichloroacetyl benzene, which compounds are unsubstituted or substituted in the benzene nucleus by alkyl groups, halide atoms, nitro groups or haloalkyl groups, like e.g. the monochloroacetyl-p-butyl benzene, the dichloroacetyl-p-butyl benzene and the trichloroacetyl-butyl benzene.

Also in said specially preferred monoketo compounds which comprise a $\pi$-electron system which is conjugating with the carbon-oxygen-double bond of the group C=O and in which, furthermore, a strongly electron attracting substituent is bonded to the carbon atom in the neighbour position to said carbonyl group, said carbonyl group can be a part of a chromophore and when the adduct between said carbonyl compound and the anion of an oxa acid is formed, then the light absorption of said adduct is shifted in the visible range or the ultraviolet range, compared with the light absorption of the corresponding free keto compound. Furthermore, it is possible that said specially preferred monoketo compounds comprise a fluorescent group and in this case the fluorescence of the adduct of the keto compound with the anion of the oxa acid differs from the corresponding fluorescence of the free keto compound, e.g. when the adduct is formed either a fluorescence of a corresponding free keto compound is quenched or in a not fluorescing free keto compound a fluorescence is induced. Specially preferred monoketo compounds of formula I can as well either comprise a fluorescent group or the carbonyl group thereof can be a part of a chromophore.

A preferred example for a monoketo compound of formula I in which the carbonyl group is a part of a chromophore, are the azo keto compounds which correspond to the following formula II

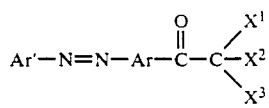

wherein the radicals

Ar and Ar' are independently from each other substituted or unsubstituted aromatic ring systems, comprising one or more aromatic nuclei or substituted or unsubstituted heterocyclic ring systems of aromatic character which comprise one or more nuclei and wherein $X^1$, $X^2$ and $X^3$ are independently from each other hydrogen atoms, alkyl groups, alkenyl groups, alkinyl groups, aryl groups, fluorine atoms, chlorine atoms, bromine atoms, iodine atoms or nitro groups, with the provision that, however, at least one of the substituents $X^1$, $X^2$ and $X^3$ is a strongly electron attracting substituent selected from the group comprising fluorine atoms, chlorine atoms, bromine atoms or nitro groups and the light absorption in the visible range or the ultraviolet range of the adduct of the keto compound of formula II with the anion of an oxa acid is shifted compared with the light absorption in the visible range or the ultraviolet range of the corresponding free keto compound of formula II.

In said azo keto compounds of formula II and also in the azo compounds of formula XIII the residues Ar and Ar' are preferably independently from each other aromatic ring systems selected from the group comprising benzene, naphthalene or anthracene or heterocyclic radicals of aromatic character selected from the group comprising thiophene, furane, pyrrole, indole, benzofurane, benzothiophene, pyridine, chinoline, pyrazine or triazine.

Furthermore in the azo compounds of formula II and in the azo compounds of formula XIII the aromatic or heteroaromatic rings or ring systems Ar and Ar' are unsubstituted or substituted and the corresponding substituents are preferably selected from the group which comprises:

halide atoms, nitro groups, thiol groups, azo groups, ether groups, carboxylic acid ester groups, hydroxy groups, esterified hydroxy groups, amino groups, alkylamino groups, in which the alkyl radicals are optionally substituted alkyl groups, dialkylamino groups in which the alkyl radicals are optionally substituted alkyl radicals, arylamino groups, respectively diarylamino groups in which the aryl radicals are optionally substituted aryl radicals, cycloalkylamino groups, respectively dicycloalkylamino groups in which the cycloalkyl groups are optionally substituted cycloalkyl groups, alkyl groups, substituted alkyl groups, alkenyl groups, substituted alkenyl groups, alkinyl groups, substituted alkinyl groups, cycloalkyl groups, substituted cycloalkyl groups, aryl groups or substituted aryl groups.

Preferred azo keto compounds of formula II in which a shifting of the light absorption in the visible range of wave lengths or in the ultraviolet range of wave lengths is observed, when said azo keto compounds interact with the anions of oxa acids and form inventive adducts with said anions of oxa acids are those azo keto compound which have the following formula III

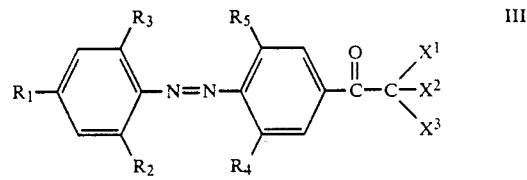

in which the substituents $R_1$, $R_2$, $R_3$, $R_4$ and $R_5$ are selected from the groups comprising hydrogen atoms, hydroxy groups, alkylether groups, arylether groups, esterified hydroxy groups, amino groups, alkylamino groups, in which the alkyl radical is unsubstituted or substituted, dialkylamino groups in which the alkyl radicals are unsubstituted or substituted, arylamino groups in which the aryl radicals are unsubstituted or substituted, nitro groups, unsubstituted alkyl groups, substituted alkyl groups, unsubstituted alkenyl groups, substituted alkenyl groups, unsubstituted alkinyl groups, substituted alkinyl groups, aromatic monocyclic or polycyclic radicals, substituted aromatic monocyclic or polycyclic radicals, heteroaromatic monocyclic or polycyclic radicals or substituted heteroaromatic monocyclic or polycyclic radicals.

Of said preferred azo compounds of formula III those are specially preferred,
in which the radicals
$R_4$ and $R_5$ are hydrogen atoms and
one or two of the radicals $R_1$, $R_2$ and $R_3$ have the meaning of hydroxy groups, etherified hydroxy groups, esterified hydroxy groups, nitro groups, amino groups, monoalkylamino groups in which the alkyl group is substituted or unsubstituted, dialkylamino groups in which the alkyl groups are substituted or unsubstituted or aryl, respectively diarylamino groups in which the aryl radicals are unsubstituted or substituted, while the remaining radicals $R_1$, $R_2$ and $R_3$ have the meaning of hydrogen atoms.

Of said preferred class of azo compounds of formula III those compounds are specially preferred,
in which the radicals
$R_2$, $R_3$, $R_4$ and $R_5$ have the meaning of hydrogen atoms and the radical
$R_1$ is a hydroxy group, an etherified hydroxy group, an esterified hydroxy group, a nitro group, an amino group, a monoalkylamino group, in which the alkyl residue is unsubstituted or substituted, a dialkylamino group, in which the alkyl groups are unsubstituted or substituted or an arylamino group in which the aryl radical is unsubstituted or substituted.

Examples for the above mentioned class of keto compounds comprised by formula III are those in which the radicals $R_2$, $R_3$, $R_4$ and $R_5$ are hydrogen atoms and the radical $R_1$ is a hydroxy group, a hydroxy group etherified with an alkyl radical having 1–20 carbon atoms, preferably an alkyl radical having 8–15 carbon atoms, for example a corresponding straight chain alkyl radical, or in which the hydroxy group is esterified with an alkane carboxylic acid, preferably an alkane carboxylic acid comprising totally 2–20 carbon atoms, preferably an alkane carboxylic acid comprising totally 6–15 carbon atoms, for example a corresponding alkane carboxylic acid, in which the alkyl group is a straight chain alkyl radical.

A further class of preferred keto compounds comprised by formula III are those,
in which the radicals
$R_2$, $R_3$, $R_4$ and $R_5$ have the meaning of hydrogen atoms and the radical
$R_1$ is an alkylamino group or a dialkylamino group in which the alkyl moieties are unsubstituted alkyl moieties or substituted alkyl moieties. Specially preferred are those compounds in which $R_1$ is a dialkylamino group comprising 2–12 carbon atoms in each of the two alkyl groups, and wherein into the alkyl chain of said alkylamino group there are optionally inserted one or more ether oxygen atoms or wherein the alkyl chain of said dialkylamino group is interrupted by an ester group. Special examples for said class of radicals $R_1$ are those, in which the radical $R_1$ is a di(alkanolamino) group, wherein each of the two hydroxy groups of the di(alkanolamine) is either etherified or esterified with a carboxylic acid, for example a alkane carboxylic acid comprising 2–10 carbon atoms.

A further object of the present invention are adducts of anions and keto compounds and said adducts are characterized in that
the anions are anions of oxa acids and that the keto compound comprises at least one keto group in which
either to the carbon atom in the neighbour position to said keto group there is bonded at least one strongly electron attracting substituent and/or
that the keto compound comprises a $\pi$-electron system which is conjugating with the carbon-oxygen-double bond of the keto group or one of the keto groups or
that the keto compound comprises at least two keto groups which are in neighbouring position to each other or in such a position to each other that the two keto groups form with the anion of the oxa acid a cyclic chelate,
with the provision that, however, in those monoketo components of the adduct, in which the keto group is bonded to an alkyl substituted benzene nucleus the group in neighbouring position to said keto group must not be a trifluoro methyl group.

The adducts of the keto compounds and the anions of the oxa acids are preferably corresponding complexes and the preferred anions of said adducts are those of the following oxa acids:

$CO_3^{--}$, $HCO_3^-$, $SO_4^{--}$, $HSO_4^-$, $SO_3^{--}$, $HSO_3^-$, $PO_4^{---}$, $HPO_4^{--}$, $H_2PO_4^-$, $ClO_3^-$, $ClO_4^-$, $BrO_3^-$, $IO_3^-$, $NO_3^-$, $NO_2^-$, $CrO_4^{--}$, $HCrO_4^-$, $Cr_2O_7^{--}$ or $HCr_2O_6^-$ or the anions of carboxylic acids, hydroxycarboxylic acids, keto-carboxylic acids, aminocarboxylic acids or the anions of peptides or the anions of organic derivatives of a phosphoric, diphosphoric or triphosphoric acid, preferably the esters of the phosphoric, the diphosphoric or triphosphoric acids, preferably an adenylic acid, the adenosine diphosphate or adenosine triphosphate.

In said adducts those keto components are preferred, which were already named before as preferred keto compounds which interact with the anions of the oxa acids, i.e. those keto compounds in which the $\pi$-electron system which is conjugating with the carbon-oxygen-double bond of the keto group is the $\pi$-electron system of an aromatic or heteroaromatic ring system or the $\pi$-electron system of a conjugated polyene, a conjugated polyine or an azo group. A specially preferred $\pi$-electron system, accordingly, is a radical Ar, which has the meaning which was already outlined before with regard to the keto compounds having the formula I.

Preferred keto components of the inventive adducts of said keto compounds with the anions of the oxa acids are accordingly the 1,2-diketo compounds having the formulae IV, IX and X stated before as well as the 1,3-diketo compounds having the formula XI stated before and, furthermore, keto compounds having isolated keto groups, like the compounds of formula XII. Further preferred keto components of the inventive adducts are those, in which the keto group is a part of a chromophore or keto components which comprise a group which has the ability of fluorescence as well as azo keto compounds.

Specially preferred keto components of the inventive adducts are those having the formula I as well as azo keto compounds having the formula II, like e.g. the azo keto compounds having the formula III. All said formulae were already stated before, and in the adducts in question the substituents and radicals have the meaning stated before, respectively the specially preferred meanings stated already before.

Several of the keto compounds which according to the present invention interact with the anions of oxa acids are already described in the prior art. New, however, are the adducts, chelates and complexes of said keto compounds with the anions of the oxa acids, respectively the processes for the preparation of said adducts, chelates and complexes.

In as far as the keto compounds which according to the present invention interact with the anions of oxa acids are not yet described in the prior art but new compounds, said keto compounds can be prepared according to processes which are well known in the prior art. For example said keto compounds can be prepared by oxidizing the corresponding secondary alcohols.

Those keto compounds in which the keto group is bonded to an aromatic or heteroaromatic ring or ring system can be prepared by acylating the corresponding aromatic, respectively heteroaromatic compounds, preferably by acylating them with a corresponding acyl halide according to the principles of the Friedel-Crafts reaction. The process for the preparation of the specially preferred keto compounds of formula I is illustrated with the following reaction scheme:

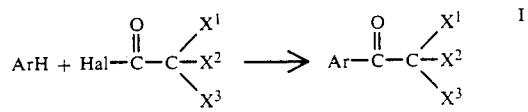

Usually said acylation reactions are performed in the presence of a Lewis acid, for example aluminum chloride.

Azo keto compounds like for instance the compounds having the formulae XIII or II stated before can be prepared by performing an azo coupling.

A further object of the present invention, accordingly, is a process for the preparation of the azo keto compounds of formula II

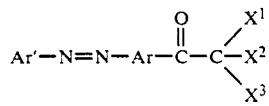

wherein the radicals

Ar and Ar' are independently from each other substituted or unsubstituted aromatic ring systems, comprising one or more aromatic nuclei or substituted or unsubstituted heterocyclic ring systems of aromatic character which comprise one or more nuclei and wherein $X^1$, $X^2$ and $X^3$ are independently from each other hydrogen atoms, alkyl groups, alkenyl groups, alkinyl groups, aryl groups, fluorine atoms, chlorine atoms, bromine atoms, iodine atoms or nitro groups, with the provision that, however, at least one of the substituents $X^1$, $X^2$ and $X^3$ is a strongly electron attracting substituent selected from the group comprising fluorine atoms, chlorine atoms, bromine atoms or nitro groups. Said azo keto compounds of formula II are prepared by either a) diazotating a primary aromatic or heteroaromatic amine of formula V

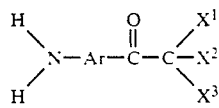

and submitting it to an azo coupling with an aromatic or heteroaromatic compound of formula VI Ar'—H                               VI and by isolating the formed azo compound of formula II or by b) diazotating a primary aromatic or heteroaromatic amine of formula VII

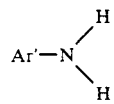

and submitting it to an azo coupling with an aromatic or heteroaromatic compound having the formula VIII

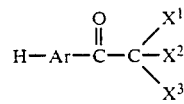

and by isolating the azo compound of formula II.

The principles of an azo coupling are well known in the prior art, specially with regard to the preparation of azo dyes.

According to the process outlined above also the preferred keto azo compounds having the formula III are prepared.

When the azo coupling illustrated in the above reaction scheme is performed then the primary amine of formula V, respectively the primary amine of formula VII is usually reacted with a nitrite in an acidic medium yielding the corresponding diazonium salt. Said diazonium salt is then reacted with the corresponding heteroaromatic compound of formula VI, respectively VIII yielding the desired final product of formula II.

A further object of the present invention is a process for the preparation of the adducts of the keto compounds with the anions of the oxa acids. According to said process the anion of the oxa acid is contacted with the corresponding keto compounds yielding the adduct.

According to a preferred embodiment of said process the anions of the oxa acids are determinated using the keto compounds which according to the present invention interact with the anions of the oxa acids. According to said process the keto compounds are contacted with the anions to be determinated.

Preferred anions of oxa acids, which can be determinated using the keto compounds are the anions which already were named before, i.e. the preferred anions of oxa acids of the preferred inventive adducts. Furthermore also in said process preferably those monoketo compounds, respectively diketo compounds are used, which were already described as preferred keto components of the inventive adducts.

The determination of the concentration of the anions of the oxa acids can be performed by using the corresponding keto compounds as ion selective component of an ion selective part which is contacted with the sample solution wherein the anions are to be determinated. A preferred example of an ion selective part is the ion selective membrane of an ion selective electrode for the determination of the concentration of anions, and said membrane contains as ion selective component the corresponding keto compounds. The process in which the adduct of the keto compound with the anion of the oxa acid is formed then occurs when the corresponding ion selective part containing the keto compound is contacted with the sample solution containing the anion to be determinated. It also is possible that already the adduct is formed, when a corresponding membrane of an ion selective electrode is contacted with anions of oxa acids which can be contained in the internal filling solution of a corresponding ion selective electrode.

Optionally the ion selective membranes of electrodes which have a selectivity for the anions to be determinated, contain further components, like carrier materials or plasticizers or also quaternary ammonium compounds which comprise at least one lipophilic aliphatic hydrocarbon chain which contains at least eight carbon atoms. Lipophilic quaternary ammonium ions are usually incorporated into corresponding ion selective membranes in order to prevent a so called cation interference, i.e. an interference of cations which are present in the sample solution in which the concentration of the anion of the oxa acid will be determined.

Examples for such lipophilic ammonium compounds are salts of ammonium compounds having at least one long aliphatic chain which contains at least 8 carbon atoms, like for instance the tridodecyl methyl ammonium chloride.

Examples for inert carrier materials which can be present in the corresponding ion selective members which contain as ion selective components the carbonyl compounds which interact with the anions of the oxa acids, are plastic materials, like polyvinyl chloride. Examples for plasticizers which can be present in such ion selective members are plasticizers which are usually used in corresponding cation selective members, like o-nitrophenyl octylether or ester plasticizers, like bis(2-ethylhexyl) sebacate. Said ion selective members including those which contain as further component a lipophilic ammonium salt can be prepared according to the processes which are described in the publication of M. E. Meyerhof, Analytical Chemistry, 1987, 59, 144.

According to a preferred embodiment of said process for the determination of the anions of oxa acids there are used such keto compounds which serve as colour indicators, in which keto compounds the keto group is a chromophore or which keto compounds comprise a fluorescent group. If said keto compounds react with the anion of an oxa acid then it is evident through a shifting of the light absorption of the corresponding compound in the visible range or in the ultraviolet range of wave lengths or it is visible through the inducing of a fluorescence or the quenching of a fluorescence.

Said carbonyl compounds which act as colour indicator can be used as component of a test device and the corresponding carbonyl compound can be present on a carrier material or in a carrier material like e.g. a carrier material of plastic material or paper. The corresponding test devices furthermore can be sensors, which change their colour in the visible range or in the ultraviolet range when they are contacted with the anions of oxa acids or in said sensor a fluorescence is provoked or quenched when they come into contact with the anions of the oxa acids.

An example for sensors are the sensors of so called optodes and in this case the sensors can be introduced into regions, the access to which is difficult and the alternation of the colour or of the fluorescence can be monitored via a transmitter, like e.g. a light transmitter.

Preferred keto compounds which are used as colour indicators, respectively as components of test devices, like e.g. sensors, are those diketo compounds which correspond to the formulae IV, IX, X, XI, XII and XIII and, furthermore, those monoketo compounds which correspond to formula I and in which keto compounds of said formulae at least one of the keto groups is a part of a chromophore or which keto compounds of the stated formulae, furthermore, comprise a group which is able to perform a fluorescence.

Specially preferred keto compounds which can be used as colour indicators, respectively as components of test devices, like e.g. as components of sensors, are those azo keto compounds having the formula II stated before, respectively the specially preferred azo keto compounds having the formula III stated before.

The corresponding colour indicators or the keto compounds which are able to perform a fluorescence can be directly added to the sample solution and through a colour change in the visible range of wave lengths or in the ultraviolet range of wave lengths or through the development of a fluorescence or a quenching of a fluorescence a qualitative or semi-quantitative determination of the anions in the test solution is possible. The corresponding indicators furthermore can be also used when titrimetric determinations of the concentration of the corresponding anions of the oxa acids can be performed.

Test devices which contain the colour indicator, respectively the fluorescence indicator on a carrier material or in a carrier material, like a plastic material or a material able to absorb liquids, like paper, can have for instance the form of test stripes. The determination of the corresponding anions of the oxa acids is then simply performed by dipping said test stripes in the sample solution.

When the corresponding test devices or tensors are contacted with the anions of an oxa acid, for instance with a liquid material containing such anions, then the changing of the colour in the visible range or the ultraviolet range or the development of a fluorescence or the quenching of a fluorescence is to be observed. Also here the degree of the change of the colour, respectively the alternation of the fluorescence, enables the person performing the test to determinate quantitatively or semi-quantitatively the concentration of the anion of the oxa acids in the sample solution.

According to a specially preferred embodiment of the invention the test means are the sensors of so called optodes, which are introduced into regions which can be reached only with difficulty, and, as outlined above, the colour change or the alternation of the fluorescence of the sensor is then observed through a transmitter, like e.g. a light transmitter. Such optodes are used in the clinical field in order to determinate in regions to which the access is difficult, like e.g. in the stomach, the intestines, the veins or the arteries, the concentration of the anions of oxa acids.

Preferred anions of oxa acids, which can be determinated using the keto compounds, are the anions mentioned before. Specially preferred anions are the carbonate anions and the bicarbonate anions. Accordingly the sensors of the above mentioned optodes for instance can be used for the determination of the concentration of carbon dioxide in blood.

A further object of the present invention is the use of those keto compounds which according to the present invention selectively interact with the anions of oxa acids as liquid crystals. In said field of application such keto compounds are preferred in which larger parts of their molecular structure are able to form a planar structure, like e.g. the diketo compounds having the formulae IX, X or XII stated before or the corresponding azo compounds having the formulae XIII and II stated before.

The present invention will be further by the following not limitative examples.

EXAMPLE 1

In this example monoketo compounds which correspond to the generic formula

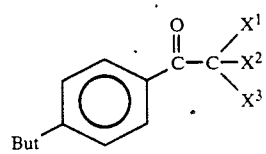

were investigated.

In said formula But is a n-butyl group.

1, 2 or 3 of the radicals $X^1$ through $X^3$ have the meaning of chlorine atoms and the remaining radicals $X^1$ through $X^3$ are hydrogen atoms.

Accordingly, the following compounds were investigated:

the monochloroacetyl-p-butyl benzene, which in the following will be abbreviated as MCABB, the dichloroacetyl-p-butyl benzene, which in the following will be abbreviated as DCABB, the trichloroacetyl-p-butyl benzene, which in the following will be abbreviated as TCABB.

All three tested ketones were able to form adducts with carbonate anions. It could be seen from the absorption spectrum in the ultraviolet range of wave lengths and also from the nuclear magnetic resonance, i.e. from the $^{13}$CNMR, that during the formation of the adduct of the free carbonyl compound with the carbonate anion the carbonyl group of the monoketo compound disappeared.

FIG. 1 of the drawing shows the $^{13}$CNMR spectrum of the trichloroacetyl-p-butyl benzene.

Figure 2:
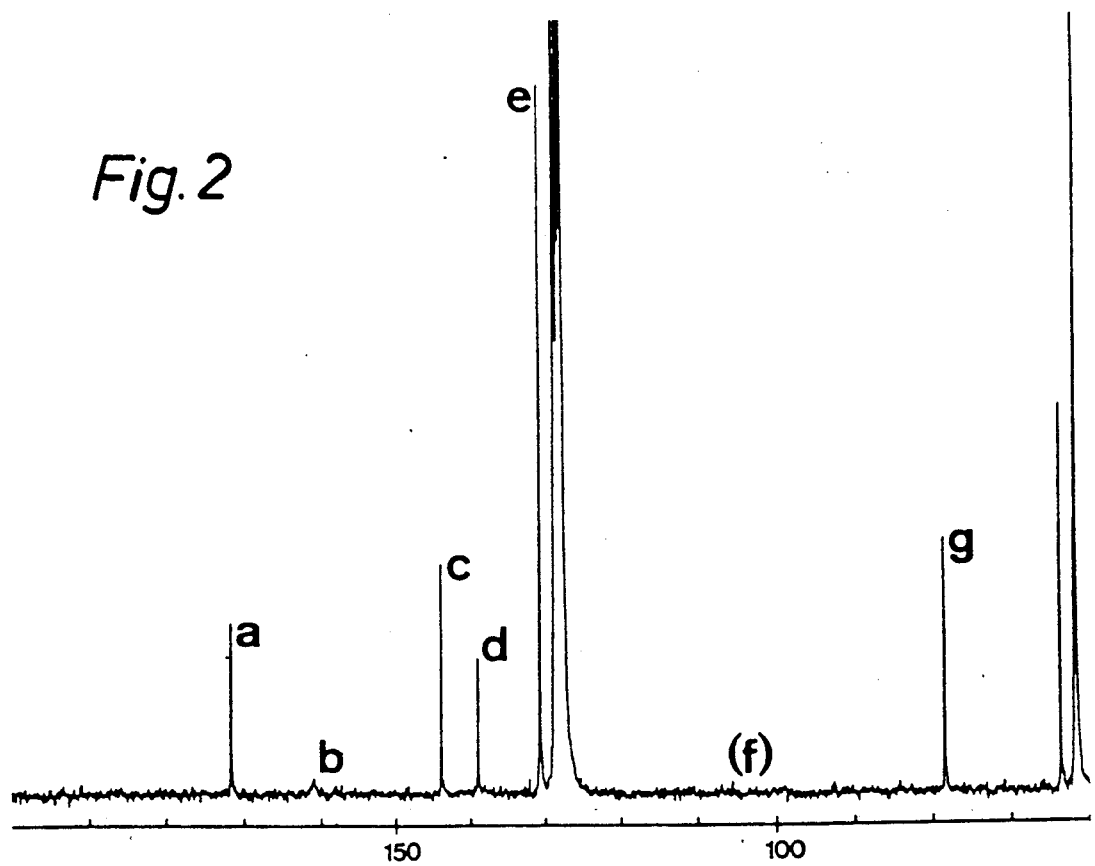

FIG. 2 of the drawing shows the $^{13}$CNMR spectrum of the adduct of the carbonate anion with said trichloroacetyl-p-butyl benzene. It can be seen from FIG. 2 that in said spectrum a new signal occurs at 78,5 ppm and said signal is the signal of the group which was yielded through the adduct formation on the carbonyl group. Furthermore a comparison of FIG. 1 of the drawing with FIG. 2 of the drawing shows the chemical shifting of the corresponding signals.

EXAMPLE 2

According to said example a 1,2-diketo compound which corresponds to the generic formula IX stated before was investigated. Said compound was the 3,5-ditert.butyl-obenzochinone having the following formula

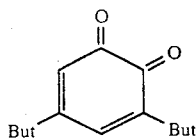

wherein both groups But are tertiary butyl groups.

Figure 3:
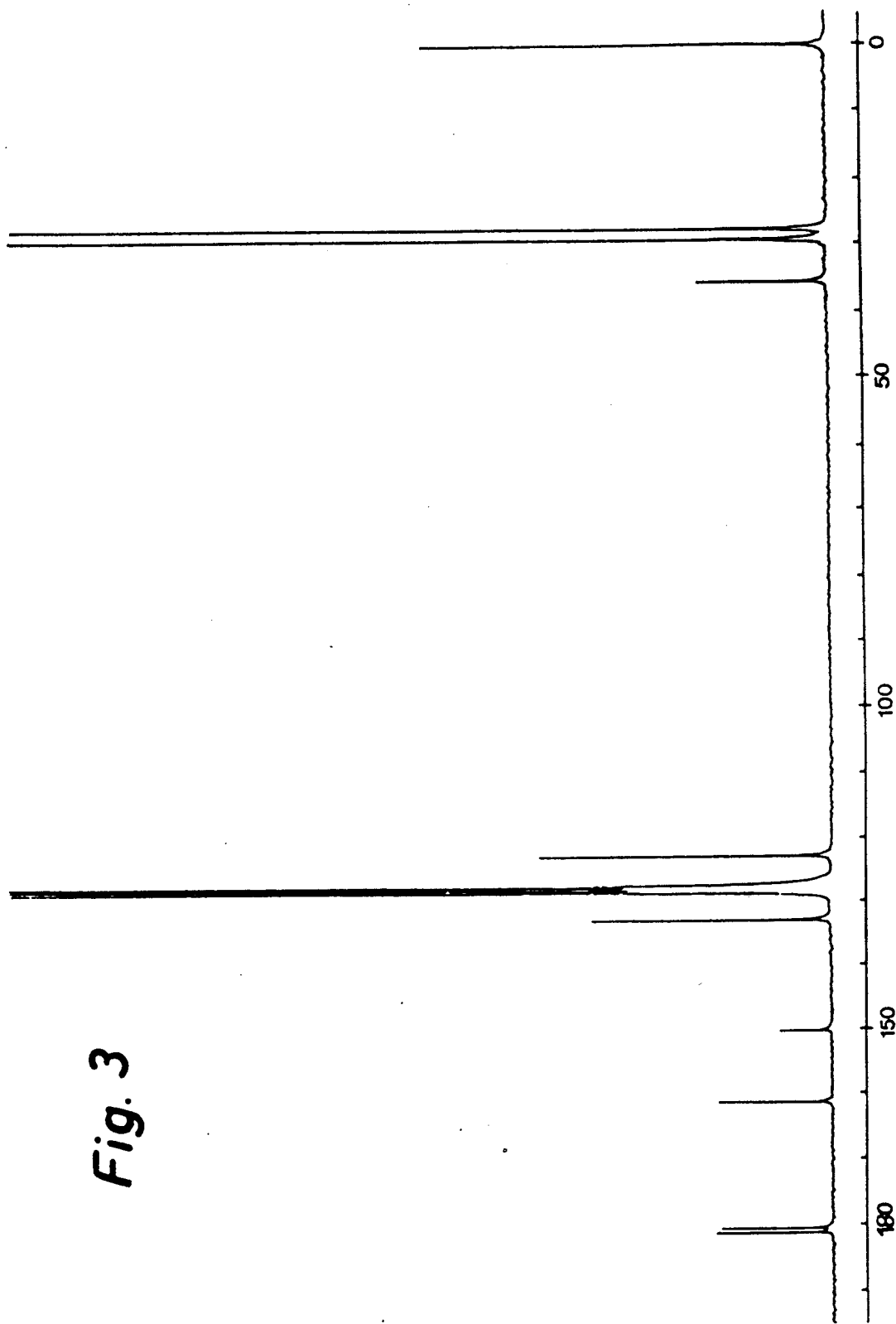

The $^{13}$CNMR spectrum of said benzochinone is illustrated in FIG. 3 of the drawing. In said figure the two signals of the carbonyl groups at about 180 ppm can be clearly seen.

Figure 4:
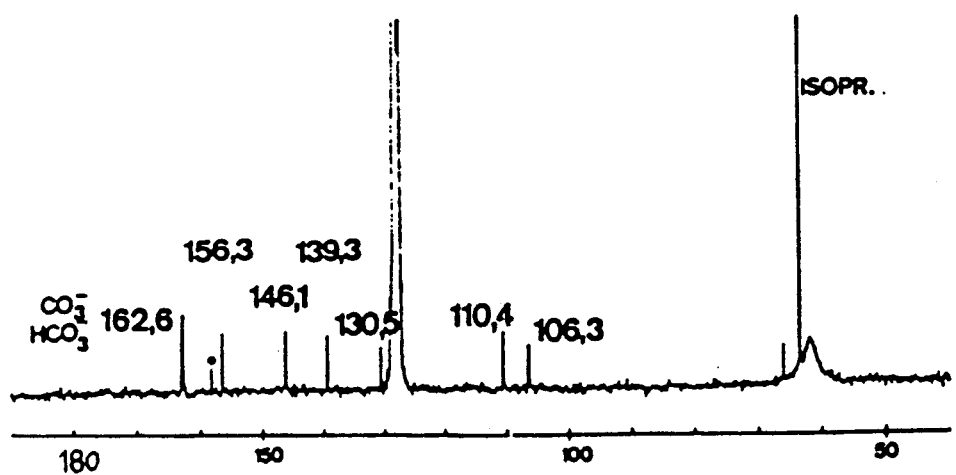

FIG. 4 of the drawing shows the carbonate adduct on said benzochinone. When said FIG. 4 is compared with FIG. 3 then there can be seen that the two signals at about 180 ppm of the free carbonyl groups have disappeared. New signals of the adducts of said carbonate anions with the carbonyl groups in the neighbouring position can be seen in said FIG. 3. The new signals are to be found at 106.3 ppm and 110.4 ppm.

EXAMPLE 3

The monoketones described in example 1 and the diketones described in example 2 were contacted with perchlorate anions and phosphate anions and sulfate anions respectively. Also here a comparison of the absorption spectra in the ultraviolet range and in the visible range showed significant alternations of the absorption between the corresponding free carbonyl compound and the adduct with the stated anions.

In the following examples 4 through 8 the preparation of azo keto compounds is described which all correspond to the generic formula IIIa.

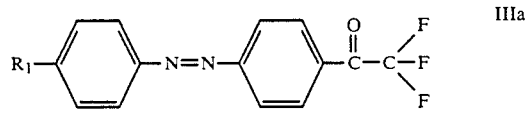

EXAMPLE 4

Preparation of the 4-trifluoroacetyl-4'-hydroxy-azobenzene

The compound named in the title corresponds to the above state formula IIIa and in said compound the residue $R_1$ is a hydroxy group.

The starting material used for the preparation of said azo keto compound was the p-trifluoroacetylaniline, which is described in the publication of K. J. Klabunde and Dr. D. J. Burton, in J. Org. Chem. 35 (1970), page 1711 and following pages.

A suspension of 2.84 g (15.00 mmol) of the p-trifluoroacetyl-aniline was stirred in 45 ml of 1-n hydrochloric acid at 25° C. during one hour and thereby all of the amino compound was dissolved in the acidic solution.

The solution had a pale yellow colour, it was filtered and cooled in an ice water mixture to a temperature of 5° C. and thereafter 1.03 g (15.000 mmol) of sodium nitrite were added. Thereby the diazonium salt was produced and the solution turned yellow.

1.41 g (15.00 mmol) of phenol were dissolved in 60 ml of a 1-n sodiumacetate solution. The aqueous solution was added to the yellow solution of the diazonium salt. Within a short time (less than 5 min.) orange crystals precipitated from the solution and after the solution was left for two hours the crystals were filtered off. Said crystals were washed with 200 ml of water and thereafter dried for two days at a temperature of 40° C.

3.90 g (13.25 mmol) of the final product named in the title were recovered. Said red needles had a melting point of 132°–133° C. The yield corresponds to 88% of the theoretical yield.

The infrared spectrum (CHCl$_3$) shows the absorption of the group —COCF$_3$ of said product at 1715 cm$^{-1}$.

The NMR data are as follows: $^1$H-NMR(300 MHz, CDCl$_3$), 10.50(s, 1H, OH); 8.20–8.23(m, 2H); 7.90–8.02(m, 4H); 6.98–7.01(m, 2H).

The mass spectrum of said product yielded M+ m/e 294.

The chemical analysis of said products having the formula C$_{14}$H$_9$.N$_2$O$_2$F$_3$ gave the following results: Calculated: C=57.15; H=3.08; N=9.52%. Found: C=57.00; H=2.91; N=9.28%.

EXAMPLE 5

Preparation of the 4-trifluoroacetyl-4'-dodecyl-azobenzene

The compound named in the title corresponds to formula IIIa and in it the radical $R_1$ is an alkylether group having the formula

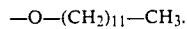

—O—(CH$_2$)$_{11}$—CH$_3$.

A mixture of 0.50 g (1.70 mmol) of the 4-trifluoroacetyl-4'-hydroxy-azobenzene which was prepared according to the process of example 4 and 15 g (80.5 mmol) of dodecanol and furthermore 10 drops of concentrated sulphuric acid (2.5 mmol) was heated for 12 hours at a temperature of 100° C.

The thin layer chromatography (developed by diethylether) showed that a small amount of the starting material had not reacted.

The cooled mixture was purified twice by performing a chromatography on a column filled with 60 g of 230-400 mesh $SiO_2$ (Fluka Company, Switzerland). As eluant a mixture of one part of dichloromethane and four parts of hexane was used.

0.42 g (0.91 mmol) of the product named in the title were recovered as red needles. The yield corresponds to 53% of the theoretical yield and said nearly pure product had a melting point of 72°-73.5° C.

Said nearly pure product was recrystallized from diethylether and so 0.35 g of a purified product were recovered which had a melting point of 73°-74° C.

In the IR spectrum (in CHCl₃) said product had, due to the presence of the groups of formula

—COCF₃ an absorption at 1715 cm⁻¹.

The nuclear magnetic resonance, i.e. ¹H-NMR (300 MHz, CDCl₃) gave: 8.19-8.22(m, 2H); 7.93-7.99(m, 4H); 6.99-7.04(m, 2H); 4.06(t, 2H); 1.83(m, 2H); 1.36-1.46(m, 18H); 0.88(t, 3H).

The mass spectrum of said product showed M⁺ m/e 462.

The chemical analysis of said product of formula $C_{26}H_{33}N_2O_2F_2$ gave the following results: Calculated: C=57.51; H=7.19; N=6.06%. Found: C=67.42; H=7.39; N=6.03%.

EXAMPLE 6

Preparation of the 4-trifluoroacetyl-4'-lauroyloxy-azobenzene

The compound named in the title corresponds to formula IIIa stated before and in said formula the radical R₁ is an ester group having the formula

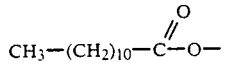

A mixture of 0.50 g (1.70 mmol) of the 4-trifluoroacetyl-4'-hydroxy-azobenzene, which had been prepared according to example 4 and of 1.00 g (4.57 mmol) of lauroylchloride in 5 ml of pyridine was stirred at a temperature of 5° C.

After said mixture had been stirred for one hour, 2 ml of diethylether were added to said red mixture and the precipitated pyridine hydrochloride was filtered off. Said precipitate was washed with 3 ml of diethylether and the washing solution was combined with the filtrate.

The combined filtrate was rapidly chromatographed, first on a column filled with 60 g 230-400 mesh $SiO_2$ (Fluka Company, Switzerland) and as eluant diethylether was used. Through said purification step the remaining pyridine was removed. Thereafter the product was chromatographed on a column which had been filled with 30 g of the $SiO_2$ stated before and the eluant was a mixture of one part of methylene chloride and three parts of hexane. Through said purification step residual lauric acid was removed from the product.

0.35 g of the product named in the title which had a melting point of 72°-73° C. were recovered. The yield corresponds to 43% of the theoretical yield.

Said product was recrystallized from diethylether yielding 0.27 g of the pure product as red small plates. They had a melting point of 72.5°-74° C.

In the IR spectrum (in —CHCl₃) the product had an absorption at 1715 cm⁻¹ because of the presence of the group of formula

—COCF₃.

The nuclear magnetic resonance, i.e. ¹H-NMR (300, CDCl₃) gave: 8.22-8.24(m, 2H); 7.98-8.03(m, 4H); 7.25-7.30 (m, 2H); 2.60(t, J=7.4, 2H); 1.73-1.83(m, 2H); 1.25-1.50(m, 16H); 0.89(t, J=6,7, 3H).

The mass spectrum gave M⁺, m/e=476.

The chemical analysis of said product of formula $C_{26}H_{31}N_2O_3F_3$ yielded the following results: Calculated: C=65.53; H=6.56; N=5.88%. Found: C=65.34; H=6.63; N=5.95%.

EXAMPLE 7

Preparation of the 4-trifluoroacetyl-4'-bis(2-butyryloxyethyl)amino-azobenzene

The compound named in the title corresponds to formula IIIa and in said formula the radical R₁ is a substituted dialkyl amino group having the structure

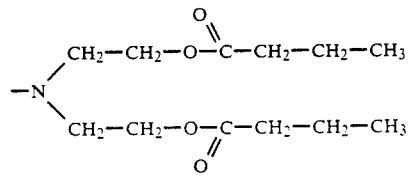

To a solution of 0.50 g (2.64 mmol) of p-trifluoroacetyl-aniline in 4 ml of acetic acid there were added 0.18 g (2.61 mmol) of sodium nitrite. Small amounts of nitrogen gas were produced and the diazonium salt was precipitated. After ten minutes the suspension which was coloured deep yellow was submitted to the further reaction steps.

Before there had been prepared from n-butyryl chloride and from N-phenyl-diethanolamine (Fluka Company, Switzerland) the N,N-bis(2-butyrylethyl)aniline.

0.93 g (2.77 mmol) of said N,N-bis(2-butyryloxyethyl)aniline were dissolved in 6 ml of acetic acid and the dark yellow suspension of the diazonium salt was added. The mixture was left for three hours and then the red solution was diluted with 50 ml of diethylether. The ether layer was extracted three times with 10 ml of water and after the evaporation of the solvent from the ethereal solution there remained a brick coloured oil which slowly crystallized on standing.

Said oil was chromatographed on a column filled with 60 g silicon dioxide (230-400 mesh $SiO_2$, Fluka Company, Switzerland). The column was eluted with diethylether and two fractions were collected.

The first fraction contained 1.36 g (2.61 mmol) of the compound named in the title and said product was isolated as fine red needles which had a melting point of 53°-56° C. Die yield of said product corresponded to 99% of the theoretical yield.

The evaporation of the solvent of the second fraction yielded 5.1 mg of an oil which consisted of the 4-trifluoroacetyl-4'-[N-(2-butyryloxyethyl)-N-(2-hydroxyethyl)-amino]-azobenzene, which was produced during said reaction as byproduct. In said byproduct, accordingly, none of the estersubstituted alkyl groups of the dialkyl amino substituent had been saponified.

The fine red needles of the product named in the title were recrystallized from 20 ml of hexane and 1.01 g of the pure product were recovered which had a melting point of 57° C.

Said pure product showed in the IR spectrum, in CHCl$_3$ an absorption at 1715 cm$^{-1}$, which is caused by the group having the formula

—COCF$_3$.

The nuclear magnetic resonance spectrum, $^1$H-NMR (300, CDCl$_3$) gave: 8.18(m, 2H); 7.91–7.96(m, 4H); 6.89(m, 2H); 4.32(t, J=6,3, 4H); 3.75(t, J=6,2, 4H); 2.29(t, J=7,4 4H); 1.58–1.70(m, 4H); 0.94(t, J=7.4 4H).

The mass spectrum yielded M$^+$ m/e 521.

The chemical analysis of said product of formula C$_{26}$H$_{30}$N$_3$O$_5$F$_3$ gave: Calculated: C=59.88; H=5.80; N=8.06%. Found: C=59.83; H=5.94; N=7.87%.

EXAMPLE 8

Preparation of the 4-trifluoroacetylazobenzene

The compound named in the title corresponds to formula IIIa and the radical R$_1$ has the meaning of a hydrogen atom.

Said compound was prepared according to the process described in example 4, however, the diazonium salt which had been prepared using the p-trifluoroacetyl-aniline as starting material now was coupled with benzene.

EXAMPLE 9

Preparation of adducts of the compounds of formula II with carbonate anions

The compounds of formula II, for example the compounds of formula III, respectively IIIa, have lipophilic properties and the adducts of carbonate anions and said products as well have lipophilic properties. Because of this the carbonate adducts were prepared using a carbonate which itself also has some lipophilic properties.

The used carbonate was the bis(tridodecylmethyl ammonium)carbonate which is described in the publication of M. E. Meyerhoff, E. Pretsch, D. H. Welti and W. Simon in Anal. Chem. 59 (1987), page 144 and the following pages. Said carbonate is a nearly colourless oil which is easily dissolvable in most of the organic solvents.

The adducts were prepared by mixing the corresponding azo keto compound of formula II with the lipophilic carbonate salt in the presence of a solvent.

The following carbonate adducts were prepared:
an adduct with the 4-trifluoroacetyl-4'-dodecyloxyazobenzene, the preparation of which is described in example 5;
the adduct with the 4-trifluoroacetyl-4'-bis(2-butyryloxyethyl)amino-azobenzene, the preparation of which is described in example 7.

Through the interaction between the carbonate anions with the carbonyl group of said compounds of formula IIIa the conjugation of the carbonyl group with the aromatic system was interrupted. In accordance with what had been expected, accordingly, the light absorption of the carbonate adduct was shifted, compared with the light absorption of the free carbonyl compound, in the direction of shorter wave lengths, i.e. through the formation of the carbonate adduct a hypsochromic shifting occurred.

In the following tables I and II the maximum of the absorption at a wave length stated in nm are given for the free carbonyl compound of formula IIIa as well as for the corresponding addition product between the carbonyl compound of formula IIIa and the carbonate anion. In column A the wave length of the maximum of the absorption of the free carbonyl compound is stated and directly beside it in brackets the extinction coefficient is given.

In column B the wave length of the peak of the absorption maximum of the corresponding carbonate adduct, as well stated in nm, is given and in brackets immediately thereafter again the extinction coefficient of said carbonate adduct.

In column C of tables I and II the shifting of the absorption maximum of the carbonate adduct in the direction of shorter wave lengths is stated in nm, compared with the absorption maximum of the free carbonyl compound of formula IIIa.

TABLE I

| | Free carbonyl compound of example 5 and its carbonate adduct | | |
|---|---|---|---|
| Solvent | A | B | C |
| acetone | 360(26000) | 348(30900) | −12 |
| diethyl-ether | 373(30900) | 352(31600) | −21 |
| hexane | 372(32100) | 347(29400) | −25 |

TABLE II

| | Free carbonyl compound according to example 7 and its carbonate adduct | | |
|---|---|---|---|
| Solvent | A | B | C |
| acetone | 452(27100) | 408(31100) | −44 |
| diethyl-ether | 445(34400) | 397(31500) | −48 |
| hexane | 437(34700) | 395(31600) | −42 |

What is claimed is:

1. An adduct of an anion of an oxa acid and a keto compound having the formula II $$Ar'-N=N-Ar-\overset{O}{\underset{\|}{C}}-C\begin{pmatrix}X^1\\X^2\\X^3\end{pmatrix} \qquad II$$

wherein
the radicals Ar and Ar' are selected independently from the following ring systems containing at least one aromatic nucleus:
(a) aromatic systems selected from the group consisting of substituted or unsubstituted benzene, substituted or unsubstituted naphthalene, substituted or unsubstituted anthracene; and
(b) substituted and unsubstituted heterocyclic systems selected from the group consisting of substituted or unsubstituted thiophene, substituted or unsubstituted furane, substituted or unsubstituted pyrrole, substituted or unsubstituted indole, substituted or unsubstituted benzofurane, substituted or unsubstituted benzothiophene, substituted or unsubstituted pyridine, substituted or unsubstituted quinoline, substituted or unsubstituted pyrazine, and substituted or unsubstituted triazine;

in which ring systems the substituents are selected from the group consisting of hydrogen, halo, nitro, thiol, azo, ether, carboxylic acid ester, hydroxy, amino, alkylamino, dialkylamino, arylamino, diarylamino, cycloalkylamino, dicycloalkylamino, alkyl, alkenyl, alkinyl, cycloalkyl, and aryl; and $X^1$, $X^2$ and $X^3$ are selected independently from the group consisting of hydrogen, alkyl, alkenyl, alkinyl, aryl, fluorine, chlorine, bromine, iodine and nitro, provided that at least one of $X^1$, $X^2$ and $X^3$ is fluorine, chlorine, bromine or nitro, further provided that the keto compound is capable of interacting with an anion of an oxa acid to shift the light absorption in the visible or ultraviolet range of the adduct compared with the light absorption in the visible or ultraviolet range of the corresponding free carbonyl group of formula II.

2. An adduct according to claim 1 wherein both radicals Ar and Ar' comprise aromatic systems.

3. An adduct according to claim 1 wherein both radicals Ar and Ar' comprise heterocyclic systems.

4. An adduct according to claim 1 wherein one of radicals Ar and Ar' comprises an aromatic system and the other comprises a heterocyclic system.

5. An adduct according to claim 1 wherein at least two of $X^1$, $X^2$ and $X^3$ are selected from fluorine, chlorine, bromine, iodine and nitro.

6. An adduct according to claim 1 wherein the anion of the oxa acid forming the adduct with the keto compound is selected from the group consisting of $CO_3^{--}$, $HCO_3^-$, $SO_4^{--}$, $HSO_4^-$, $SO_3^{--}$, $HSO_3^-$, $PO_4^{---}$, $HPO_4^{--}$, $H_2PO_4^-$, $ClO_3^-$, $ClO_4^-$, $BrO_3^-$, $IO_3^-$, $NO_3^-$, $NO_3^-$, $NO_2^-$, $CrO_4^{--}$, $HCrO_4^-$, $Cr_2O_7^{--}$, and $HCr_2O_7^-$.

7. An adduct according to claim 1 wherein the adduct corresponds to the following formula III

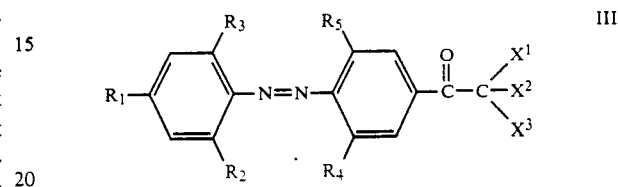

wherein the substituents $R_1$, $R_2$, $R_3$, $R_4$ and $R_5$ are selected independently from the group consisting of hydrogen, hydroxy, alkyl ether, aryl ether, amino, alkylamino, dialkylamino, arylamino, nitro, alkyl, alkenyl, alkinyl, aromatic monocyclic, aromatic polycyclic, heteroaromatic monocyclic, and heteroaromatic polycyclic.

* * * * *

UNITED STATES PATENT AND TRADEMARK OFFICE
CERTIFICATE OF CORRECTION

PATENT NO. : 5,037,968

DATED : August 6, 1991

INVENTOR(S) : Wilhelm Simon and Erno Pretsch

It is certified that error appears in the above-identified patent and that said Letters Patent is hereby corrected as shown below:

Column 26, claim 7, line 1, after the word "the", insert --keto compound of the--.

Signed and Sealed this

Thirtieth Day of March, 1993

Attest:

STEPHEN G. KUNIN

Attesting Officer

Acting Commissioner of Patents and Trademarks